(12) United States Patent
Pless et al.

(10) Patent No.: US 8,903,499 B2
(45) Date of Patent: Dec. 2, 2014

(54) NEUROSTIMULATOR SYSTEM APPARATUS AND METHOD

(71) Applicant: Autonomic Technologies, Inc., Redwood City, CA (US)

(72) Inventors: Benjamin D. Pless, Atherton, CA (US); Karen Tsuei, Redwood City, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 0 days.

(21) Appl. No.: 13/897,828

(22) Filed: May 20, 2013

(65) Prior Publication Data

US 2013/0310895 A1    Nov. 21, 2013

Related U.S. Application Data

(60) Provisional application No. 61/649,535, filed on May 21, 2012.

(51) Int. Cl.
*A61N 1/00* (2006.01)
*A61N 1/372* (2006.01)

(52) U.S. Cl.
CPC ......... *A61N 1/37223* (2013.01); *A61N 1/37229* (2013.01)
USPC .......................................... 607/60

(58) Field of Classification Search
CPC ... A61N 1/37252; A61N 1/37223; A61N 1/08
USPC .......................................... 607/60
See application file for complete search history.

(56) References Cited

U.S. PATENT DOCUMENTS 8,265,768 B2 * 9/2012 Klostermann et al. .......... 607/60

* cited by examiner

*Primary Examiner* — George Manuel
(74) *Attorney, Agent, or Firm* — Tarolli, Sundheim, Covell & Tummino LLP

(57) ABSTRACT

An apparatus (10) for applying stimulation therapy to a patient includes an implantable medical device (20) and a remote controller (50*a*) for inductively powering the medical device and communicating with the medical device. The remote controller (50*a*) includes an improved coil configuration to improve communication performance between the remote controller (50*a*) and an implanted medical device (20).

22 Claims, 4 Drawing Sheets

NEUROSTIMULATOR SYSTEM APPARATUS AND METHOD

RELATED APPLICATIONS

This application claims the benefit of U.S. Provisional Application Ser. No. 61/649,535, filed on May 21, 2012.

FIELD OF THE INVENTION

The invention relates generally to systems, devices, and methods for using an implantable medical device to deliver therapy to a patient. More specifically, this invention relates to improved coil configuration to improve communication performance between an external remote control device and an implanted medical device.

BACKGROUND OF THE INVENTION

Primary headaches are debilitating ailments that afflict millions of individuals worldwide. The specific pathophysiology of primary headaches is not known. Known causes of headache pain include trauma, vascular defects, autoimmune deficiencies, degenerative conditions, infections, drug and medication-induced causes, inflammation, neoplastic conditions, metabolicendocrine conditions, iatrogenic conditions, musculoskeletal conditions, and myofacial causes. In many situations, however, even though the underlying cause of the headache may be identified and treated, the headache pain itself may persist.

Recent clinical studies in treatment of headaches have targeted the manipulation of sphenopalatine (pterygopalatine) ganglion (SPG), a large, extra-cranial parasympathetic ganglion. A ganglion is a mass of neural tissue found in some peripheral and autonomic nerves. Ganglia are located on the roots of the spinal nerves and on the roots of the trigeminal nerve. Ganglia are also located on the facial, glossopharyngeal, vagus and vestibulochoclear nerves. The SPG is a complex neural ganglion with multiple connections, including autonomic, sensory, and motor connections. The SPG includes parasympathetic neurons that innervate, in part, the middle cerebral and anterior cerebral blood vessels, the facial blood vessels, and the lacrimal glands.

The maxillary branch of the trigeminal nerve and the nerve of the pterygoid canal (also known as the vidian nerve which is formed by the greater and deep petrosal nerves) send neural projections to the SPG. The fine branches from the maxillary nerve (pterygopalatine nerves) form the sensory component of the SPG. These nerve fibers pass through the SPG and do not synapse. The greater petrosal nerve carries the preganglionic parasympathetic axons from the superior salivary nucleus, located in the pons, to the SPG. These fibers synapse onto the postganglionic neurons within the SPG. The deep petrosal nerve connects the superior cervical sympathetic ganglion to the SPG and carries postganglionic sympathetic axons that again pass through the SPG without any synapsing in the SPG.

The SPG is located within the pterygopalatine fossa. The pterygopalatine fossa is bounded anteriorly by the maxilla, posteriorly by the medial plate of the pterygoid process and greater wing of the sphenoid process, medially by the palatine bone, and superiorly by the body of the sphenoid process. The lateral border of the pterygopalatine fossa is the pterygomaxillary fissure, which opens to the infratemporal fossa. Various clinical approaches have been used to modulate the function of the SPG in order to treat headaches, such as cluster headaches or chronic migraines. These approaches vary from lesser or minimally invasive procedures (e.g., transnasal anesthetic blocks) to procedures or greater invasiveness (e.g., surgical ganglionectomy). Other procedures of varying invasiveness include those such as surgical anesthetic injections, ablations, gamma knife procedures, and cryogenic surgery. Although most of these procedures can exhibit some short term efficacy in the order of days to months, the results are usually temporary and the headache pain eventually reoccurs.

SUMMARY OF THE INVENTION

The invention relates to systems, devices, and methods for using an implantable medical device ("IMD") to deliver therapy to a patient. According to one aspect, the invention relates to an IMD for delivering electrical stimulation to a peripheral, central or autonomic neural structure. In this aspect, the IMD may be a neurostimulator for treating primary headaches, such as migraines, cluster headaches, trigeminal autonomic cephalalgias and/or many other neurological disorders, such as atypical facial pain and/or trigeminal neuralgias.

In one embodiment, an IMD and an associated handheld remote controller ("RC") each may have an operating memory for storing a programmable operating instructions and data, both input and recorded, that govern the operation of each respective device. The IMD and RC each may also include processing hardware, associated with the operating memory, for executing the programmable operating instructions in accordance with the input and recorded data. According to one aspect, the IMD may receive, from the RC, operating instructions, data, or both operating instructions and data, that at least partially govern the therapies applied by the IMD. The IMD administers therapy in accordance with stimulation parameters stored on the IMD. The stimulation parameters may be programmed into the IMD in a variety of manners. For example, the stimulation parameters may be programmed via a programming system with the RC acting as an interface or wand.

The ability of an inductively powered IMD to work at increasing implant depths depends on the ability to transmit greater amounts of power into the IMD from the external RC while still being able to detect the faint telemetry signals from the implanted device. In some RCs, a single coil of wire (also known as an inductive antenna, a loop antenna, a transmit/receiver coil or antenna, etc) is used for transmitting power and commands as well as for receiving telemetry from the IMD. The RC transmits power to the IMD while simultaneously receiving the telemetry signals from the IMD. As the IMD is planted physically further away from the RC, the power signal from the RC necessarily gets proportionally larger and the telemetry signal consequently gets proportionally smaller.

Accordingly, the present invention relates to an apparatus for coupling a RC or similar external device to an IMD (or other device that needs to be powered at a distance, and has a telemetry link). The apparatus includes multiple coils in the RC to allow for sensitive detection of telemetry from the IMD while cancelling out the large power signal used for inductively powering the IMD.

According to one aspect, the invention relates to an apparatus for applying stimulation therapy to a patient. The apparatus includes an implantable medical device and a remote controller for inductively powering the implantable medical device and communicating with the implantable medical device. The remote controller includes a transmit coil for transmitting a transmit signal to the implantable medical device and a receiver coil for receiving a telemetry signal from the implantable medical device. The receiver coil is configured to cancel out at least a portion of the transmit signal.

DESCRIPTION OF EMBODIMENTS

Figure 1:
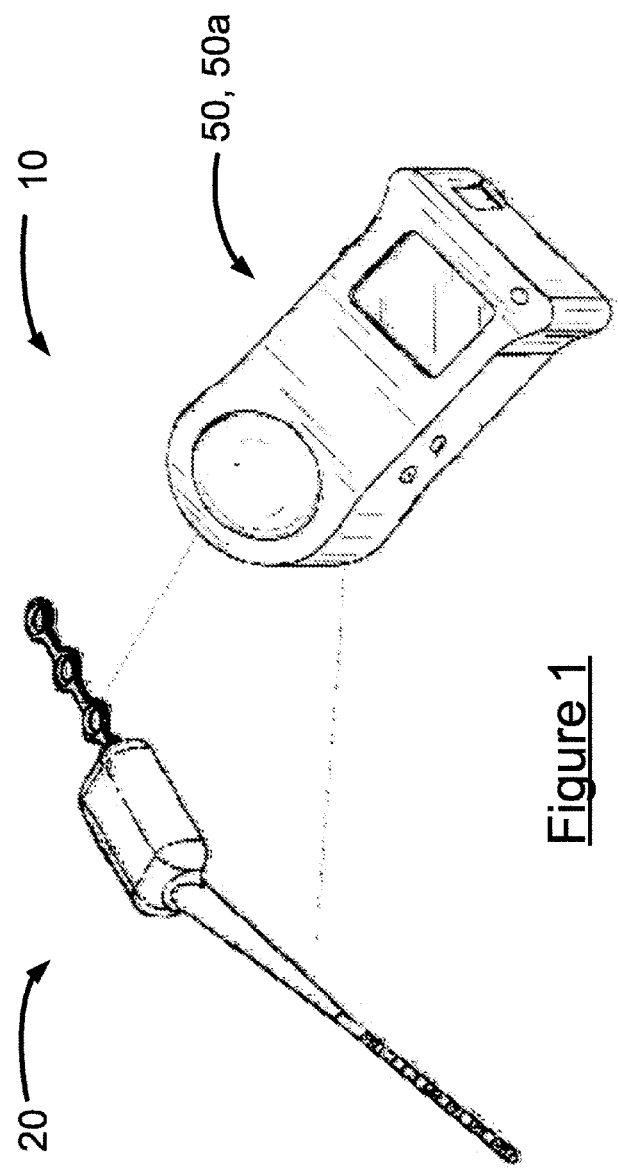
FIG. 1 is a schematic illustration of the devices that form a portion of a system for delivering therapy using an IMD.

FIG. 1 illustrates, by way of example, a medical device forming a portion of a system 10 that can be implemented in accordance with the invention. Referring to FIG. 1, according to one aspect of the invention, the system 10 includes an implantable medical device ("IMD") 20 and a handheld remote controller ("RC") 50, 50a for interfacing with the IMD 20 to provide power to and control operation of the IMD 20. In this description, the term "implantable" is meant to describe that the medical device is configured for in vivo placement in the patient by surgical or other means.

In the example embodiment illustrated in FIG. 1, the IMD 20 is an implantable neurostimulator. The IMD 20 may, for example, be a neurostimulator for delivering electrical stimulation to a peripheral, central, or autonomic neural structure. In this implementation, the IMD 20 may be a neurostimulator for treating primary headaches, such as migraines, cluster headaches, trigeminal autonomic cephalalgias and/or other neurological disorders, such as atypical facial pain and/or trigeminal neuralgias. Examples of these types of neurostimulators are shown and described in pending U.S. patent application Ser. Nos. 12/688,524 and 12/765,712, the disclosures of which are hereby incorporated by reference in their entireties.

The RC 50, 50a illustrated in FIG. 1 is for controlling and powering the IMD 20 which, in this example embodiment, is a neurostimulator. The RC 50, 50a of FIG. 1 is therefore adapted to control and power a neurostimulator IMD 20. The RC 50, 50a could, however, control and power alternative devices capable of receiving wireless control and power signals. The RC 50, 50a may, for example, have some or all of the features shown and described in U.S. Provisional Application Nos. 61/578,337 and 61/578,415, the disclosures of which are hereby incorporated by reference in their entireties.

Figure 2:
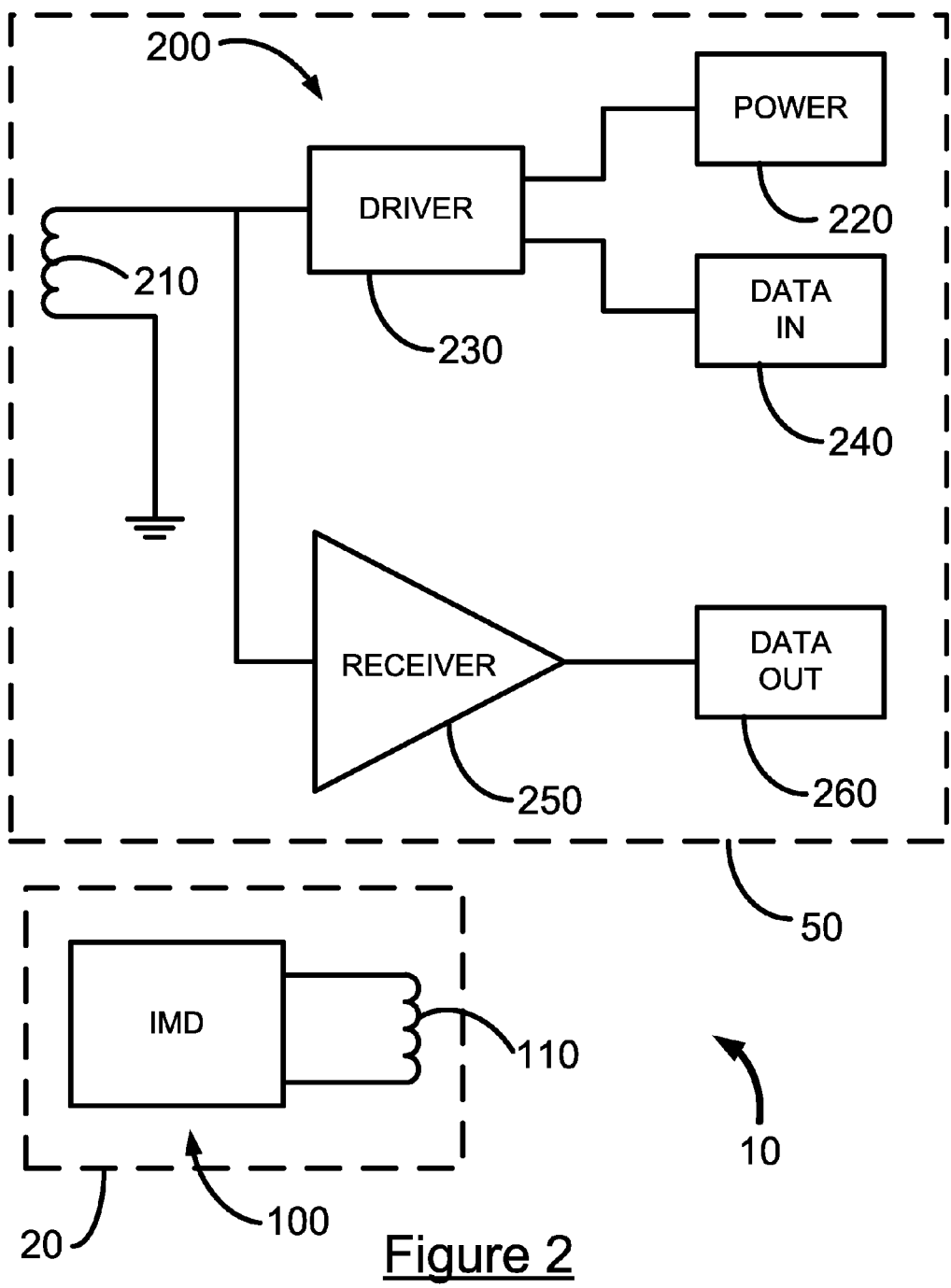
FIG. 2 shows an implementation of a RC using a single coil to transmit and receive signals to an IMD.

FIG. 2 illustrates schematically an example configuration of the system 10 of FIG. 1. In the example configuration of FIG. 2, the IMD 20 includes circuitry 100 that is adapted to perform the functions of that particular IMD. In the illustrated example, the IMD circuitry 100 is adapted to perform the neurostimulation functions of the IMD 20. The circuitry 100 also includes a transmit/receive coil 110 that is operatively connected to the circuitry 100.

In the example configuration of FIG. 2, the RC 50 includes circuitry 200 that is configured to provide power and control signals to the IMD 20 and to receive feedback signals from the IMD. The circuitry 200 includes a single power/transmit/receive coil 210 that is connected to a driver circuit 230 and to a receiver circuit 250. The driver circuit 230 is operatively connected to a power supply 220, such as a rechargeable or replaceable battery power supply, and to a data source 240, such as processing hardware and/or operating memory of the RC 50. The receiver circuit 250 is configured and arranged to supply data 260 to components of the RC 50, such as processing hardware and/or operating memory.

In operation of the example configuration of the system 10 shown in FIG. 2, the driver circuit 230 utilizes electrical power from the power supply 220 to energize and drive the coil 210 to transmit a power signal to the IMD 20. The driver circuit 230 transmits the power signal at a strength and frequency sufficient to power the IMD 20, given the relative distance between the RC 50 and the implanted IMD. The power signal generated by the RC 50 excites coil 110 of the IMD 20 which induces electrical current in the coil 110, thus powering the IMD 20 via induction. This induced electrical current supplies power to the IMD 20 which, in turn, utilizes the power to apply therapy (e.g., neuromodulation therapy) to the patient.

The circuitry 200 of the RC 50 is also operable to provide commands to the IMD 20 for controlling its operation. In response to the received data 240, the driver circuit 230 of the RC 50 is adapted to modulate a control signal that is transmitted to the IMD 20 via the coil 210. The circuitry 100 of the IMD 20 receives the signal via the coil 110 acting as an antenna, and applies neurostimulation therapy according to the instructions/data contained therein.

The IMD 20 also utilizes the induced power received from the RC 50 to transmit via the coil 110 any communication and/or feedback signals to the RC 50. To do this, the IMD 20 circuitry 100 can selectively change the impedance of the coil 110 to create a telemetry signal that is transmitted to the RC 50.

The circuitry 200 of the RC 50, while powering and controlling the IMD 20, is further operable to simultaneously receive the communication and/or feedback signals from the IMD 20. The telemetry signal is picked up by the coil 210 of the RC 50 and supplied to the receiver circuit 250. The receiver circuit 250 filters and amplifies the telemetry signal and supplies the communication and/or feedback contained in the telemetry signal as the data 260 to the processing hardware and/or operating memory of the RC 50.

Figure 3:
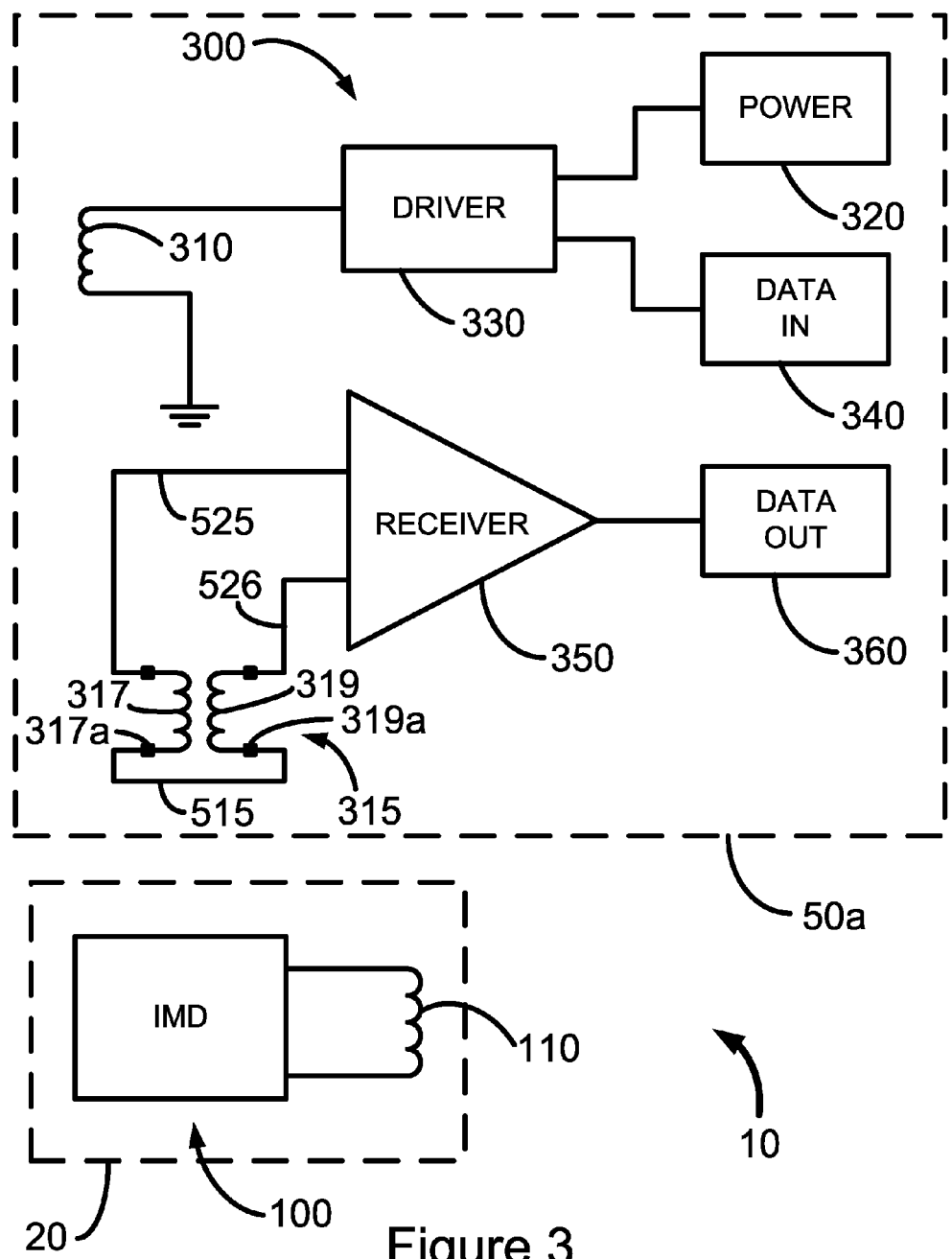
FIG. 3 shows an implementation of the subject invention using a separate transmit coil and receiver coil, where the receiver coil is comprised of two coils.

In the configuration 200 of FIG. 2, the driver circuit 230 generates a very large power signal that is transmitted via the coil 210 at the same time that the receiver circuit 250 is trying to detect a very faint telemetry signal received via the same coil 210. This power/transmit/receive multiple functionality of the coil 210 is disadvantageous because the strong power signal can interfere with the detection of the comparatively weak telemetry signal. In the embodiment of FIG. 3, the system 10 has a configuration that is designed to help overcome these disadvantages and to help improve the transmit/receive performance of the system.

FIG. 3 illustrates schematically a configuration of the RC 50a of the system 10 of FIG. 1. In the system 10 of FIG. 3, the IMD 20 can be identical to the IMD of the system shown in FIG. 2, thus including IMD circuitry 100 and IMD coil 110. The IMD 20 therefore can be similar or identical in function and design to that which is described above in reference to the IMD of FIG. 2.

According to the invention, the RC 50a of the system 10 illustrated in FIG. 3 has circuitry 300 that differs from the circuitry 200 of the RC 50 illustrated in FIG. 2. The circuitry 300 is configured to provide power and control signals to the IMD 20 and to receive signals from the IMD. In the embodiment of FIG. 3, the RC circuitry 300 includes a power coil 310 and a separate receiver coil 315.

The power coil 310 is connected to a driver circuit 330. The driver circuit 330 is operatively connected to a power supply 320, such as a rechargeable or replaceable battery power supply. The driver circuit 330 is also operatively connected to a data source 340, such as processing hardware and/or operating memory of the RC 50a.

The receiver coil 315 is operatively connected to the receiver circuit 350. The receiver circuit 350 is configured and arranged to supply data 360 to components of the RC 50a, such as processing hardware and/or operating memory. In the system 50a of FIG. 3, the receiver coil 315 includes two sub-coils 317 and 319. According to the invention, the sub-coils 317 and 319 are configured and geometrically aligned such that common signals received by both sub-coils cancel each other out and, therefore, the receiver 350 does not register the canceled signal. In this manner, the receiver coil 315 of RC 50a is configured to cancel the power signal from the transmit coil, which allows the receiver 350 to register and receive the telemetry signal from the IMD 20 with little or no interference from the power signal.

The coils 310 and 315 of the RC 50a can have many alternative constructions. In one example construction of the RC 50a, the transmit coil 310 can be made of a comparatively heavy Litz wire and can carry peak currents of about 5 to 20 amps at a voltage of around 200 to 500 volts. The transmit coil 310 can have relatively few turns—for example in the range of 20 to 80 turns. The receiver coil 315 is made a fine single strand wire and does not carry high current. Since, however, the receiver coil 315 can have comparatively large numbers of turns—for example measured in the hundreds—it can produce voltages that can be in excess of 1000 volts. Thus, construction of the receiver coil 315 can require heavy build wire for its construction.

Figure 4A:
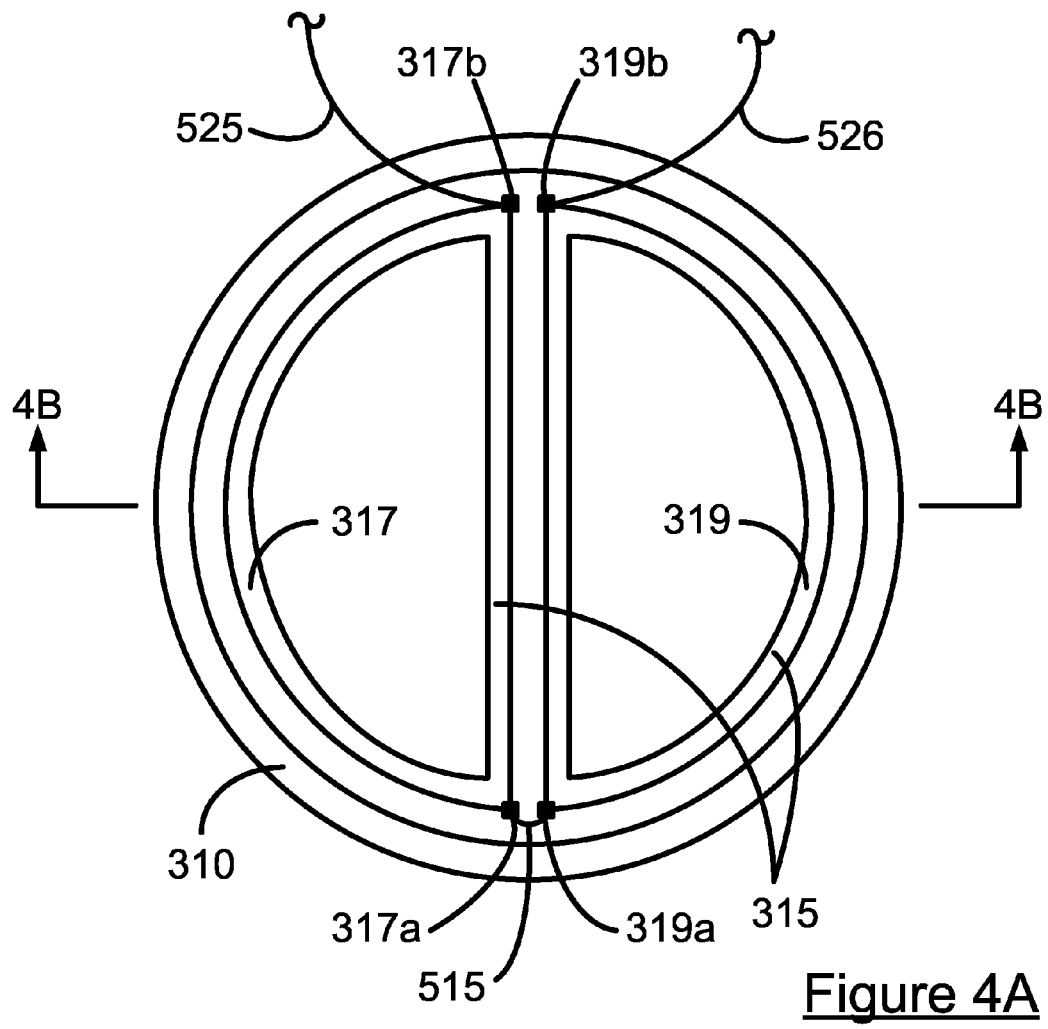
FIG. 4A shows a possible geometric configuration of the coils.
Figure 4B:
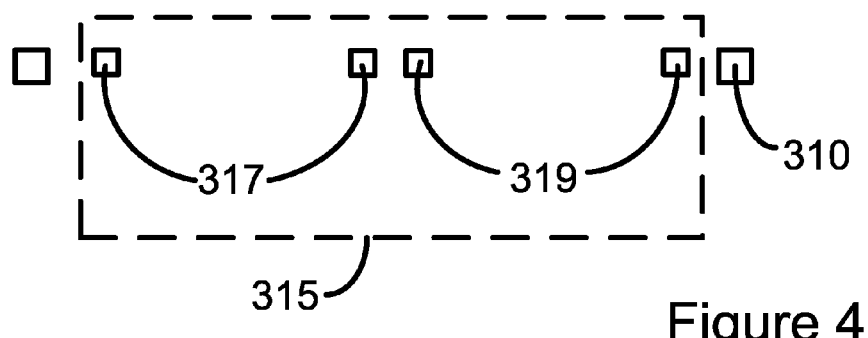
FIG. 4B shows a cross section of FIG. 4A.

Referring to FIGS. 4A and 4B, the transmit coil 310 and receive coil 315 of the RC 50a are configured and arranged such that the receiver coil 315 cancels out the power signal generated by the transmit coil 310.

The transmit coil 310 and the receiver coil 315 are geometrically and spatially arranged relative to each other within the RC 50a so that the sub-coils 317 and 319 each receive the identical power signal from the transmit coil. More specifically, the receiver sub-coils 317 and 319 are arranged such that the wave of the power signal generated by the transmit coil 310 excites both sub-coils equally (e.g., in terms of frequency, amplitude, angle, etc.) and simultaneously to the greatest extent possible through their relative geometric and spatial configurations within the RC 50a.

Electrically, the receiver coil 315, is configured such that the positive terminal 317a of sub-coil 317 is connected to the positive terminal 319a of sub-coil 319, as shown in FIG. 3. The geometric and electrical configuration of the receiver sub-coils 317 and 319 are thus excited in an equal and opposite manner and thus cancel out the signal received from the transmit coil 310. The other terminals of sub-coils 317 and 319 are connected to the receiver 350.

An example embodiment of one such suitable geometric relationship is illustrated schematically in FIGS. 4A and 4B. In this embodiment, the transmit coil 310 has a circular coil configuration. The sub-coils 317 and 319 of the receiver coil 315 are have a "D" shaped configuration and are arranged symmetrically in a mirror-imaged fashion and nested centrally within the transmit coil 310. The positive terminals 317a and 317b of the of sub-coils 317 and 319 are electrically connected by wire 515 and the other (negative) terminals 317b and 319b are connected to the receiver 350 via wires 525 and 526, respectively. With this arrangement, the sub-coils 317 and 319 can be effectively wound in opposite directions.

The degree of signal cancellation can be fine-tuned by adjusting the position of the receiver coil 315 relative to the transmit coil 310 and monitoring the signal received via the wires 525 and 526. When the monitored signal strength reaches its lowest level, the position of the receiver coil 315 relative to the transmit coil 310 within the RC 50a is ideal. The receiver coil 315 can be fixed at this ideal position so that future signal detection performed by the RC 50a is done with optimal transmit signal cancellation.

From the above, those skilled in the art will appreciate that the configuration of the receiver coil 315 in the RC 50a can effectively cancel reception of the power signal from the transmit coil 310. Those skilled in the art will also appreciate that the configuration of the receiver coil 315 can have little or no effect on receiving the telemetry signal from the IMD 20 coil 110. This is because, as discussed above, the effective cancellation of a signal (e.g., the power signal) by the receiver coil 315 relies on precise spatial and geometric positioning of the receiver sub-coils 317 and 319 relative to the transmitting coil. Since the IMD 20 is implanted according to patient's anatomy, the position of the IMD coil 110 relative to the receiver coil 315 is variable and constantly changing. Thus, cancelation of the IMD telemetry signal would be rare, sporadic, and coincidental, and would be alleviated simply by re-positioning the RC 50a.

The telemetry signal from the IMD 20 coil 110 is only cancelled out by the RC 50a receiver coil 315 if the IMD 20 coil 110 is perfectly aligned with the RC 50a receiver coil 315. In an actual implant, it can be very difficult to get the IMD 20 coil 110 and the RC 50a receiver coil 315 to be perfectly aligned. And, if that should occur, it is easy for the user to move the RC 50a slightly to get the two coils to be slightly misaligned.

To increase the sensitivity of the receiver coil 315 to faint telemetry signals from the IMD 20 coil 110, the number of windings on both sub-coils 317 and 319 can be increased. However, the receiver coil 315 remains insensitive to the power signal on the transmit coil 310 since the power signal from the transmit coil 310 is cancelled out by the sub-coils 317 and 319. This enables power to be sent to a more deeply implanted IMD 20 without adversely affecting the ability of the receiver 350 to detect a faint telemetry signal from the IMD coil 110.

The embodiment of FIGS. 4A and 4B illustrates a symmetrical configuration of the sub-coils 317 and 319. The signal canceling features of the receiver coil 315 do not, however, necessarily rely on this symmetrical configuration. The RC 50a could, for example, have circuitry 300 configured such that the sub-coils of the receiver coil 315 have asymmetrical configurations. The sub-coils, while asymmetrical, can be configured to cancel the signal generated by transmit coil 310.

For example, the sub-coil 317 may be configured to be physically smaller than the sub-coil 319. To compensate for this, the sub-coil 317 could be configured to have a greater number of turns/windings. Additionally or alternatively, the sub-coil 317 could be positioned relative to the sub-coil 319 and relative to the transmit coil 310 such that the power signal from the transmit coil 310 acts more directly or with a greater signal strength on the smaller sub-coil 317. As a result, the excitation of the asymmetrical sub-coils 317 and 319 may nevertheless cancel the transmit signal, thus enabling a more effective reception of the telemetry signal from the IMD 110.

From the above description of the invention, those skilled in the art will perceive improvements, changes and modifications. Such improvements, changes and modifications within the skill of the art are intended to be covered by the appended claims.

What is claimed is:

1. An apparatus for applying stimulation therapy to a patient, the apparatus comprising:
   an implantable medical device; and
   a remote controller for inductively powering the implantable medical device and communicating with the implantable medical device, the remote controller comprising:
   a transmit coil for transmitting a transmit signal to the implantable medical device; and
   a receiver coil for receiving a telemetry signal from the implantable medical device, the receiver coil being configured to cancel out at least a portion of the transmit signal, wherein the receiver coil comprises at least two sub-coils geometrically configured to cancel out at least a portion of the transmit signal.

2. The apparatus recited in claim 1, wherein the sub-coils are arranged in a symmetrical fashion.

3. The apparatus recited in claim 2, wherein the sub-coils comprise first and second D-shaped coils.

4. The apparatus recited in claim 3, wherein the transmit coil has a circular configuration and the first and second D-shaped coils are nested within the circular transmit coil.

5. The apparatus recited in claim 1, wherein the sub-coils have positive ends electrically connected with each other.

6. The apparatus recited in claim 1, wherein:
   the remote controller is adapted to excite via the transmit coil a transmit/receive coil of the implantable medical device;
   the implantable medical device is adapted to transmit via the transmit/receive coil a telemetry signal; and
   the remote controller is further adapted to receive the telemetry signal via the receiver coil.

7. The apparatus recited in claim 1, wherein the remote controller further comprises a receiver operatively connected to the receiver coil, the receiver being adapted to receive a telemetry signal from the implantable medical device.

8. The apparatus recited in claim 1, wherein the remote controller further comprises a power driver adapted modulate the energy of the transmit coil in response to the received data.

9. The apparatus recited in claim 8, wherein the power driver is adapted to drive the transmit coil at a suitable frequency to transmit power to a transmit/receive coil of the implantable medical device to power the implantable medical device.

10. The apparatus recited in claim 8, wherein the power driver is adapted to modulate the signal on the transmit coil to send commands to the implantable medical device.

11. The apparatus recited in claim 1, wherein the implantable medical device comprises a transmit/receive coil and is adapted to selectively change the impedance of the transmit/receive coil to transmit a telemetry signal, the remote controller being adapted to receive, filter, and amplify the telemetry signal.

12. The apparatus recited in claim 1, wherein the sub-coils have asymmetrical configurations.

13. The apparatus recited in claim 12, wherein the sub-coils are configured with an unequal number of windings to compensate for their asymmetrical configurations.

14. The apparatus recited in claim 12, wherein the sub-coils are shaped geometrically and/or spatially to compensate for their asymmetrical configurations.

15. A remote controller for inductively powering and communicating with an implantable medical device, the remote controller comprising:
    a transmit coil; and
    a receiver coil having a configuration and position relative to the transmit coil that cancels out at least a portion of a transmit signal transmitted by the transmit coil, wherein the receiver coil comprises at least two sub-coils.

16. The remote controller recited in claim 15, wherein the sub-coils are arranged in a symmetrical fashion.

17. The remote controller recited in claim 15, wherein the sub-coils comprise first and second D-shaped coils.

18. The remote controller recited in claim 15, wherein the transmit coil has a circular configuration and the first and second D-shaped coils are nested within the circular transmit coil.

19. The remote controller recited in claim 15, wherein the sub-coils have positive ends electrically connected with each other.

20. The remote controller recited in claim 15, wherein the sub-coils have asymmetrical configurations.

21. The remote controller recited in claim 20, wherein the sub-coils are configured with an unequal number of windings to compensate for their asymmetrical configurations.

22. The remote controller recited in claim 20, wherein the sub-coils are shaped geometrically and/or spatially to compensate for their asymmetrical configurations.

* * * * *